United States Patent
Jubran et al.

(10) Patent No.: US 7,501,216 B2
(45) Date of Patent: *Mar. 10, 2009

(54) AZINE-BASED CHARGE TRANSPORT MATERIALS

(75) Inventors: Nusrallah Jubran, St. Paul, MN (US); Zbigniew Tokarski, Woodbury, MN (US); Kam W. Law, Woodbury, MN (US)

(73) Assignee: Samsung Electronics Co., Ltd., Suwon-si (KR)

( * ) Notice: Subject to any disclaimer, the term of this patent is extended or adjusted under 35 U.S.C. 154(b) by 287 days.

This patent is subject to a terminal disclaimer.

(21) Appl. No.: 10/804,719

(22) Filed: Mar. 19, 2004

(65) Prior Publication Data

US 2004/0241562 A1   Dec. 2, 2004

Related U.S. Application Data

(60) Provisional application No. 60/483,727, filed on Jun. 30, 2003, provisional application No. 60/474,543, filed on May 30, 2003.

(51) Int. Cl.
G03G 5/047 (2006.01)

(52) U.S. Cl. .................. 430/58.35; 430/72; 399/159; 564/249

(58) Field of Classification Search ............ 430/58.35, 430/58.4, 58.45, 72; 399/159; 564/249
See application file for complete search history.

(56) References Cited

U.S. PATENT DOCUMENTS

| | | | |
|---|---|---|---|
| 4,297,426 A | 10/1981 | Sakai et al. | |
| 4,415,640 A | 11/1983 | Goto et al. | |
| 4,420,548 A | 12/1983 | Sakai et al. | |
| 4,786,571 A | 11/1988 | Ueda | |
| 4,957,838 A | 9/1990 | Aruga et al. | |
| 5,128,227 A | 7/1992 | Monbaliu et al. | |
| 6,066,426 A | 5/2000 | Mott et al. | |
| 6,099,996 A | 8/2000 | Yanus et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,350,553 B2 | 2/2002 | Srinivasan | |
| 6,670,085 B2 | 12/2003 | Jubran et al. | |
| 6,689,523 B2 | 2/2004 | Law et al. | |
| 6,696,209 B2 | 2/2004 | Law et al. | |
| 7,261,987 B2 * | 8/2007 | Jubran et al. | 730/75 |
| 2003/0104294 A1 | 6/2003 | Law et al. | |
| 2003/0113132 A1 | 6/2003 | Law et al. | |
| 2003/0113643 A1 | 6/2003 | Law et al. | |
| 2003/0113644 A1 | 6/2003 | Law et al. | |
| 2003/0138712 A1 | 7/2003 | Law et al. | |
| 2003/0198880 A1 | 10/2003 | Law et al. | |
| 2003/0219662 A1 | 11/2003 | Jubran et al. | |
| 2004/0265717 A1 * | 12/2004 | Tokarski et al. | 430/58.35 |

FOREIGN PATENT DOCUMENTS

| JP | 62-116943 | 11/1985 |
|---|---|---|
| WO | WO00/63748 | 10/2000 |

OTHER PUBLICATIONS

Diamond, A.S., ed., *Handbook of Imaging Materials*, Marcel Dekker, Inc.,NY (1991), pp. 395-396.*
U.S. Appl. No. 60/483,726, filed Jun. 30, 2003.*
Patent Abstracts of Japan English-language abstract describing JP 07-149704, copyright 1995, JPO.*
Donald Bethell et el, "Oligomeric Bis(1,3-Indandiylidene)azine: Preparation, Electochemical and spectroscopic properties, and implications for the use of polyazines as conducting matericals," J. Chem Soc. Perkin Trans. 2, (6) 1081-1086 (1996).

* cited by examiner

*Primary Examiner*—Janis L Dote
(74) *Attorney, Agent, or Firm*—DLA Piper LLP US

(57) ABSTRACT

This invention includes an improved organophotoreceptor having an electrically conductive substrate and a photoconductive element on the electrically conductive substrate where the photoconductive element comprises:
(a) a charge transport material having the formula

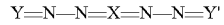

where Y and Y' comprise, each independently, a 9-fluorenylidene group; and X is a conjugated linking group that allows the delocalization of pi electrons over at least Y and Y', such as a 1,2-ethanediylidene group, a 1,4-phenylenedimethylidyne group, a 2,4-cyclohexadienylidene group, a 2,5-cyclohexadienylidene group, a bicyclohexylidene-2,5,2',5'-tetraene group, a bicyclohexylidene-2,4,2',4'-tetraene group, or a combination thereof; and (b) a charge generating compound. Corresponding electrophotographic apparatuses and imaging methods are described.

19 Claims, No Drawings

AZINE-BASED CHARGE TRANSPORT MATERIALS

CROSS REFERENCE TO RELATED APPLICATIONS

This application claims priority to copending U.S. Provisional Patent Application Ser. No. 60/474,543 to Jubran et al., filed on May 30, 2003, and entitled "Azine-Based Charge Transport Materials," incorporated herein by reference; and U.S. Provisional Patent Application Ser. No. 60/483,727 to Jubran et al., filed on Jun. 30, 2003, and entitled "Azine-Based Charge Transport Materials," incorporated herein by reference.

FIELD OF INVENTION

This invention relates to organophotoreceptors suitable for use in electrophotography and, more specifically, to an organophotoreceptor having charge transport materials comprising two flurenone azine groups.

BACKGROUND

In electrophotography, an organophotoreceptor in the form of a plate, disk, sheet, belt, drum or the like having an electrically insulating photoconductive element on an electrically conductive substrate is imaged by first uniformly electrostatically charging the surface of a photoconductive element, and then exposing the charged surface to a pattern of light. The light exposure selectively dissipates the charge in the illuminated areas where light strikes the surface, thereby forming a pattern of charged and uncharged areas referred to as a latent image. A liquid toner or solid toner can then be provided in the vicinity of the latent image, and toner droplets or particles can be deposited in either the charged or uncharged areas depending on the properties of the toner to create a toned image on the surface of the photoconductive element. The resulting toned image can be transferred to a suitable ultimate or intermediate receiving surface, such as paper, or the photoconductive element can operate as the ultimate receptor for the image. The imaging process can be repeated many times to complete a single image, which can involve, for example, overlying images of distinct color components or effecting shadow images to complete a full color complete image, and/or to reproduce additional images.

Both single layer and multilayer photoconductive elements have been used. In the single layer embodiment, charge generating compound and a charge transport material selected from the group consisting of a charge transport compound, an electron transport compound, and a combination of both are combined with a polymeric binder and then deposited on the electrically conductive substrate. In the multilayer embodiments based on a charge transport compound, the charge transport compound and charge generating compound are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept these charge carriers and transport them through the charge transport layer in order to discharge a surface charge on the photoconductive element. The charge transport material can be a charge transport compound, an electron transport compound, or a combination of both. When a charge transport compound is used, the charge transport compound accepts the hole carriers and transports them through the layer in which the charge transport compound is located. When an electron transport compound is used, the electron transport compound accepts the electron carriers and transports them through the layer in which the electron transport compound is located.

SUMMARY OF THE INVENTION

This invention provides organophotoreceptors having good electrostatic properties such as high $V_{acc}$ and low $V_{dis}$.

In a first aspect, the invention pertains to an organophotoreceptor comprising an electrically conductive substrate and a photoconductive element on the electrically conductive substrate, the photoconductive element comprising:

a) a charge transport material having the following formula:

$$Y=N-N=X=N-N=Y' \quad (1)$$

where Y and Y' comprise, each independently, a 9-fluorenylidene group; and X is a conjugated linking group that allows the delocalization of the pi electrons in Formula (1) over at least Y and Y', such as a 1,2-ethanediylidene group, a 1,4-phenylenedimethylidyne group, a 2,4-cyclohexadienylidene group, a 2,5-cyclohexadienylidene group, a bicyclohexylidene-2,5,2',5'-tetraene group, a bicyclohexylidene-2,4,2',4'-tetraene group, or a combination thereof; and (b) a charge generating compound.

The organophotoreceptor may be provided, for example, in the form of a plate, a flexible belt, a flexible disk, a sheet, a rigid drum, or a sheet around a rigid or compliant drum. In one embodiment, the organophotoreceptor includes: (a) a photoconductive element comprising the charge transport material, the charge generating compound, optionally a second charge transport material, and optionally a polymeric binder; and (b) the electrically conductive substrate.

In a second aspect, the invention features an electrophotographic imaging apparatus that comprises (a) a light imaging component; and (b) the above-described organophotoreceptor oriented to receive light from the light imaging component. The apparatus can further comprise a toner dispenser. The method of electrophotographic imaging with photoreceptors containing the above noted charge transport material is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features a charge transport material having Formula (1) above.

The invention provides suitable charge transport materials for organophotoreceptors featuring a combination of good mechanical, electrostatic, and solubility properties. These photoreceptors can be used successfully with toners, such as liquid toners and dry toners, to produce high quality images. The high quality of the imaging system can be maintained after repeated cycling.

Other features and advantages of the invention will be apparent from the following description of the specific embodiments thereof, and from the claims.

DETAILED DESCRIPTION

An organophotoreceptor as described herein has an electrically conductive substrate and a photoconductive element comprising a charge generating compound and a charge transport material having two 9-fluorenone azine groups bonded together through a conjugated linking group. These charge transport materials have desirable properties as evidenced by their performance in organophotoreceptors for electrophotography. In particular, the charge transport materials of this invention have high charge carrier mobilities and good compatibility with various binder materials, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as fax machines, photocopiers, scanners and other electronic devices based on electrophotography. The use of these charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as a charge transport compound or an electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, (N,N-disubstituted) arylamines such as triaryl amines, polyvinyl carbazole, polyvinyl pyrene, polyacenaphthylene, or multi-hydrazone compounds comprising at least two hydrazone groups and at least two groups selected from the group consisting of (N,N-disubstituted)arylamine such as triphenylamine and heterocycles such as carbazole, julolidine, phenothiazine, phenazine, phenoxazine, phenoxathiin, thiazole, oxazole, isoxazole, dibenzo(1,4)dioxin, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of electron transport compounds include, for example, bromoaniline, tetracyanoethylene, tetracyanoquinodimethane, 2,4,7-trinitro-9-fluorenone, 2,4,5, 7-tetranitro-9-fluorenone, 2,4,5,7-tetranitroxanthone, 2,4,8-trinitrothioxanthone, 2,6,8-trinitro-indeno[1,2-b]thiophene-4-one, and 1,3, 7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene) thiopyran, derivatives of phospha-2, 5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene) malononitrile, (4-carbitoxy-9-fluorenylidene)malononitrile, and diethyl(4-n-butoxycarbonyl-2, 7-dinitro-9-fluorenylidene)-malonate, anthraquinodimethane derivatives such as 11,11, 12,12-tetracyano-2-alkylanthraquinodimethane and 11,11-dicyano-12, 12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl) methylene]anthrone, 1,8-dihydroxy-10-[bis(ethoxycarbonyl)methylene]anthrone, and 1-cyano-10-[bis (ethoxycarbonyl)methylene)anthrone, 7-nitro-2-aza-9-fluorenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232, 800,4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport materials described herein are especially effective at transporting charge, and in particular holes from the electron-hole pairs formed by the charge generating compound. In some embodiments, a specific electron transport compound or charge transport compound can also be used along with the charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

The improved charge transport materials described herein comprise at least two azine groups. Specifically, the improved charge transport materials have the formula:

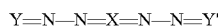

(1)

where Y and Y' comprise, each independently, a 9-fluorenylidene group; and X is a conjugated linking group that allows the delocalization of the pi electrons in Formula (1) over at least Y and Y', such as a 1, 2-ethanediylidene group, a 1, 4-phenylenedimethylidyne group, a 2, 4-cyclohexadienylidene group, a 2, 5-cyclohexadienylidene group, a bicyclohexylidene-2, 5, 2', 5'-tetraene group, a bicyclohexylidene-2, 4, 2', 4'-tetraene group, or a combination thereof.

A heterocyclic group may be any cyclic ring group that has at least a heteroatom, such as S, O, N, P, B, in the cyclic ring. Non-limiting examples of suitable heterocyclic group include an epoxy group, a thiiranyl group, an aziridinyl group, an oxetanyl group, a tertahydrofuranyl group, tetrahydrothiophenyl group, a tetrahydropyrrolyl group, a pyrrolidenyl group, a piperidinyl group, and the aromatic heterocyclic groups described below.

A conjugated linking group of this invention is any linking group that allows the delocalization of the pi-electrons in Formula (1) over at least the Y and Y' groups. Non-limiting examples of suitable conjugated linking group include a 1, 2-ethanediylidene group, a 1, 4-phenylenedimethylidyne group, a 2, 4-cyclohexadienylidene group, a 2, 5-cyclohexadienylidene group, a bicyclohexylidene-2, 5, 2', 5'-tetraene group, a bicyclohexylidene-2, 4, 2',4'-tetraene group, or a combination thereof.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4) dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, and N. Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, and N.

Substitution is liberally allowed on the chemical groups to affect various physical effects on the properties of the compounds, such as mobility, sensitivity, solubility, compatibility, stability, and the like, as is known generally in the art. In the description of chemical substituents, there are certain practices common to the art that are reflected in the use of language. The term group indicates that the generically recited chemical entity (e.g., alkyl group, alkenyl group, heterocyclic group, aromatic group, 9-fluorenylidene group, a 1, 2-ethanediylidene group, a 1, 4-phenylenedimethylidyne group, a 2, 4-cyclohexadienylidene group, a 2, 5-cyclohexadienylidene group, a bicyclohexylidene-2, 5, 2', 5'-tetraene group, a bicyclohexylidene-2, 4, 2', 4'-tetraene group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom, such as 3-ethoxylpropyl, 4-(N,N-diethylamino)butyl, 3-hydroxypentyl, 2-thiolhexyl, 1, 2, 3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N,N-disubstituted) aminophenyl, 2,4-dihydroxyphenyl, 2,4,6-trithiophenyl, 2,4, 6-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Where the term moiety is used, such as alkyl moiety or phenyl moiety, that terminology indicates that the chemical moiety is not substituted. When referring to an alkyl moiety, the term represents only an unsubstituted alkyl hydrocarbon group, whether branched, straight chain, or cyclic.

The charge transport material may or may not be symmetrical. Thus, for example, Y and Y' may be the same or different; and X group itself may or may not be symmetrical. In addition, the above-described formula for the charge transport material is intended to cover isomers.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (TEDLAR™, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodine, conductive polymers such as polypyrroles and CALGON™ conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAST™ Orange, quinacridones available from DuPont under the trade name MONASTRAL™ Red, MONASTRAL™ Violet and MONASTRAL™ Red Y, naphthalene 1,4,-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in abandoned U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as TINUVIN™ 144 and TINUVIN™ 292 (from Ciba Specialty Chemicals, Terrytown, N.Y.), hindered alkoxydialkylamines such as TINUVIN™ 123 (from Ciba Specialty Chemicals), benzotriazoles such as TINUVIN™ 328, TINUVIN™ 900 and TINUVIN™ 928 (from Ciba Specialty Chemicals), benzophenones such as SANDUVOR™ 3041 (from Clariant Corp., Charlotte, N.C.), nickel compounds such as ARBESTAB™ (from Robinson Brothers Ltd, West Midlands, Great Britain), salicylates, cyanocinnamates, benzylidene malonates, benzoates, oxanilides such as SANDUVOR™ VSU (from Clariant Corp., Charlotte, N.C.), triazines such as CYAGARD™ UV-1164 (from Cytec Industries Inc., N.J.), polymeric sterically hindered amines such as LUCHEM™ (from Atochem North America, Buffalo, N.Y.). In some embodiments, the light stabilizer is selected from the group consisting of hindered trialkylamines having the following formula:

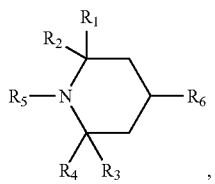

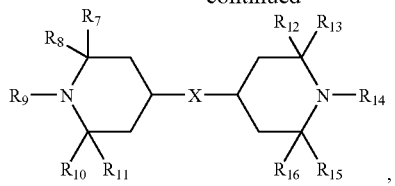

-continued where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. IUPILON™-A from Mitsubishi Engineering Plastics, or LEXAN™ 145 from General Electric); polycarbonate Z which is derived from cyclohexylidene bisphenol (e.g. IUPILON™-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET™ TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optional additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport compound can advantageously further include a UV light stabilizer. In particular, the electron transport layer generally can comprise an electron transport compound, a binder, and an optional UV light stabilizer. An overcoat layer comprising an electron transport compound is described further in U.S. patent application Ser. No. 10/396,536, which is now U.S. Pat. No. 6,890,693, to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, poly(methyl methacrylate), polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, polysilane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, which is now U.S. Pat. No. 6,890,693, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics, and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Material

As described herein, an organophotoreceptor comprises a charge transport material having the formula

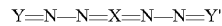

$$Y=N-N=X=N-N=Y' \qquad (1)$$

where Y and Y' comprise, each independently, a 9-fluorenylidene group; and X is a conjugated linking group that allows the delocalization of the pi electrons in Formula (1) over at least Y and Y', such as a 1, 2-ethanediylidene group, a 1, 4-phenylenedimethylidyne group, a 2, 4-cyclohexadienylidene group, a 2, 5-cyclohexadienylidene group, a bicyclohexylidene-2, 5, 2', 5'-tetraene group, a bicyclohexylidene-2, 4, 2', 4'-tetraene group, or a combination thereof.

The X group of Formula (1) clearly has at least 2 $sp^2$ hybridized carbon atoms that bond to the adjacent nitrogen atoms to complete the azine groups. The conjugated chain of the X group can be a linear chain and/or cyclic groups, which may or may not be aromatic.

With respect to Formula (1), substitution is liberally allowed, especially on X, Y, and Y'. Variation of the substituents, such as an aromatic group, an alkyl group, a heterocyclic group, and a ring group such as a benzo group, on X, Y, and Y' can result in various physical effects on the properties of the compounds, such as mobility, solubility, compatibility, stability, spectral absorbance, dispersibility, and the like, including, for example, substitutions known in the art to effect particular modifications.

In some embodiments, the conjugated linking group may be a $(C_6R_1R_2R_3R_4)_n$ group, where $C_6$ is a cyclohexadienylidene group with substituents $R_1R_2R_3R_4$; n is an integer between 1 and 20, inclusive; and $R_1$, $R_2$, $R_3$, and $R_4$, each independently, are a hydrogen, a halogen, an amino group, a nitro group, a cyano group, an alkyl group, an alkenyl group, a heterocyclic group, an aromatic group, or part of a ring group. In further embodiments, the $C_6R_1R_2R_3R_4$ group in the $(C_6R_1R_2R_3R_4)_n$ group has one of the following formulae:

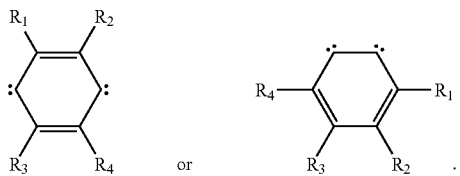

In some embodiments, the 9-fluorenylidene group may have the following formula:

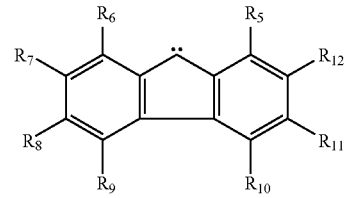

where $R_5$, $R_6$, $R_7$, $R_8$, $R_9$, $R_{10}$, $R_{11}$, and $R_{12}$, each independently, may be any substituent that does not destroy the 9-fluorenylidene ring. Furthermore, each of the substituents may be part of a ring group that can add to or expand the 9-fluorenylidene ring. Non-limiting examples of suitable substituent include a hydrogen, a halogen, a hydroxyl group, a thiol group, a carboxyl group, an amino group, a nitro group, a cyano group, an alkyl group, an alkenyl group, a heterocyclic group, an aromatic group, or part of a ring group.

Specifically, some non-limiting examples of the charge transport materials of this invention have the following formulas:

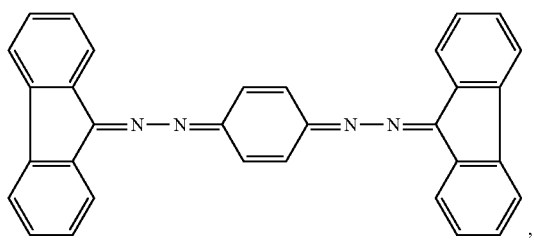

(2)

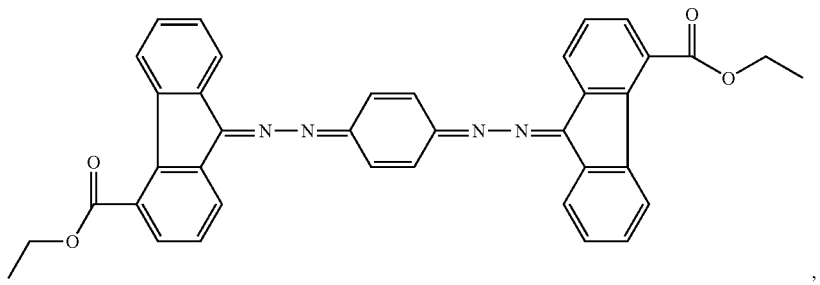

(3)

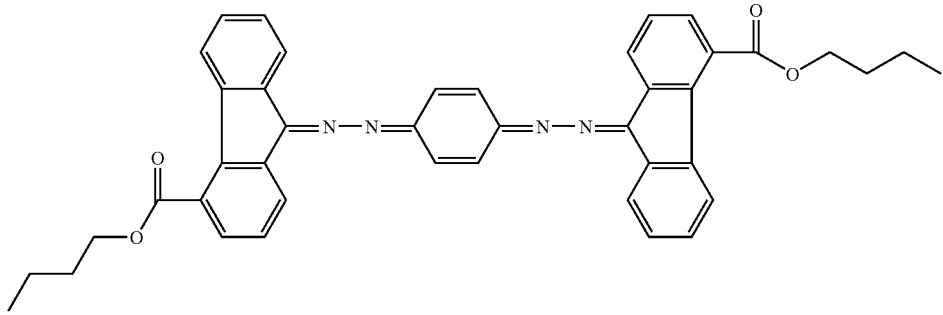

(4)

-continued
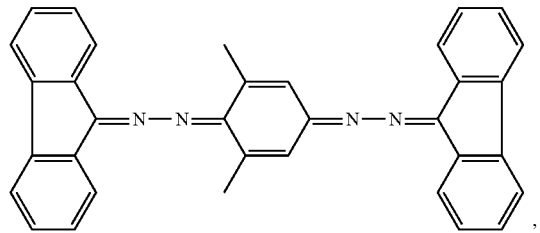
(5)
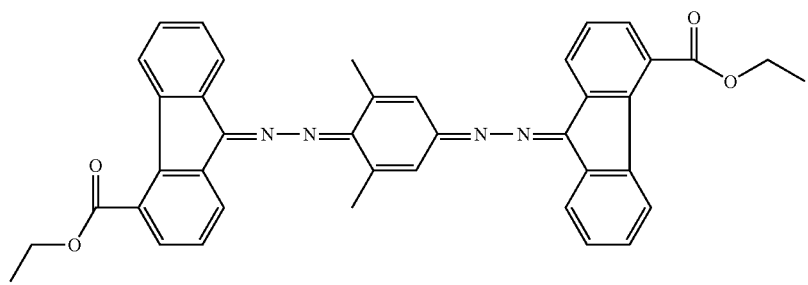
(6)
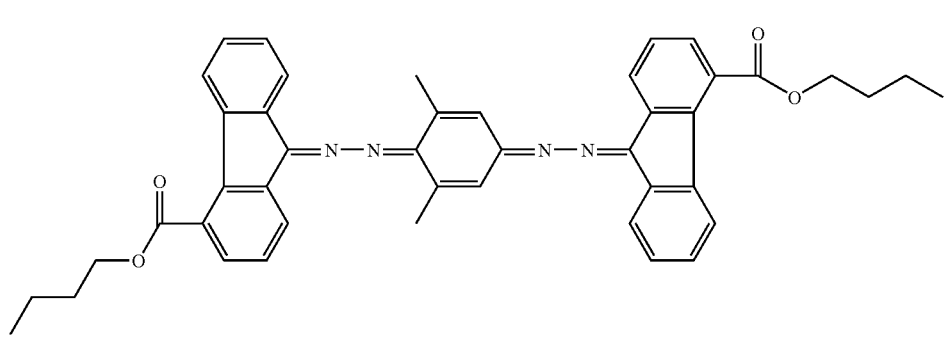
(7)
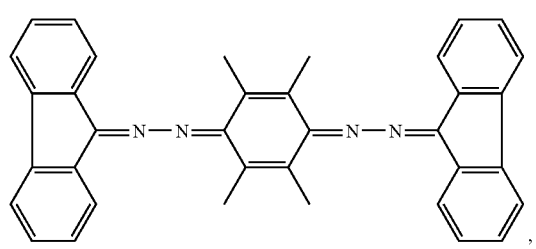
(8)
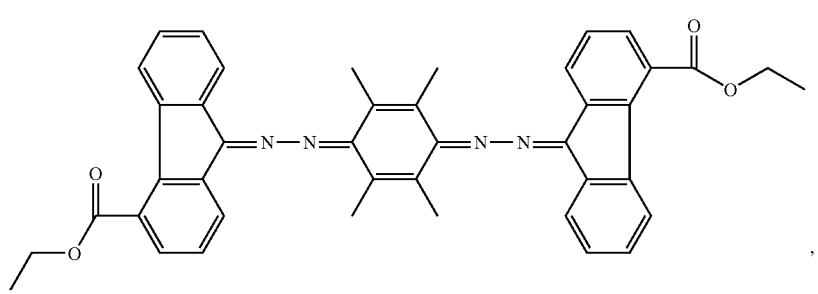
(9)

-continued

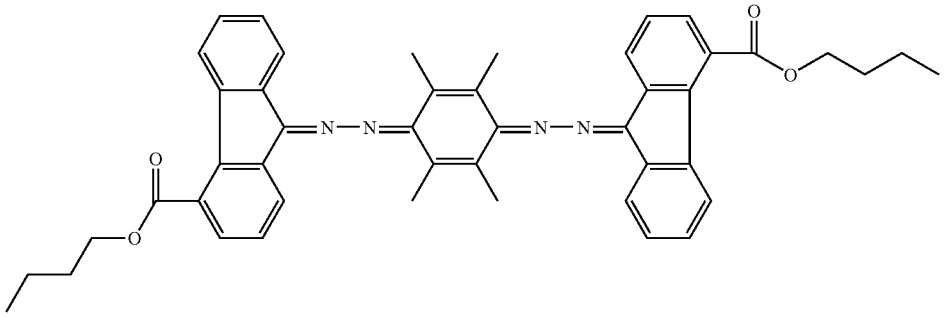
(10)

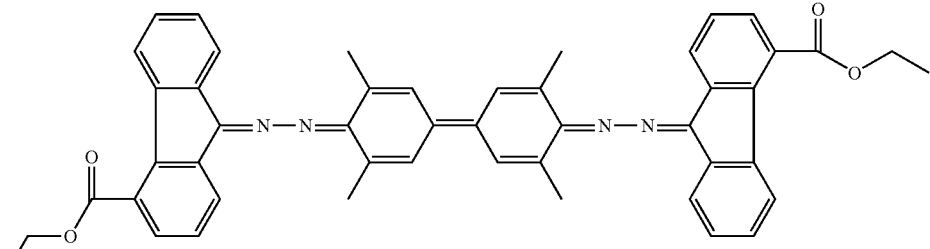
(11)

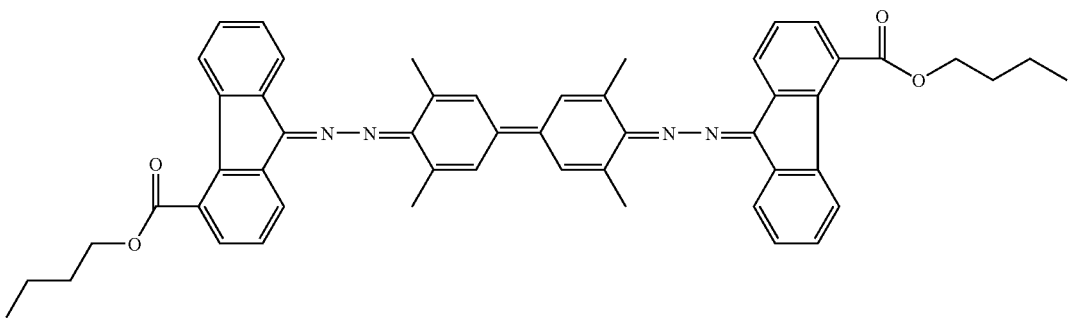
, and
(12)

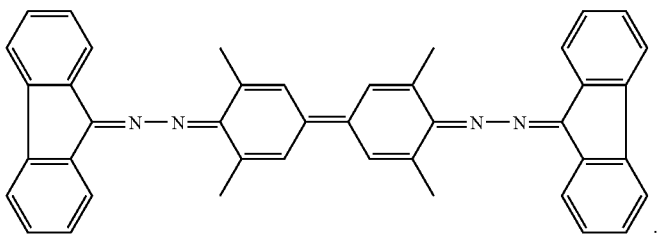
(13)

These photoreceptors can be used successfully with toners, such as liquid toners and dry toners, to produce high quality images. The high quality of the images can be maintained after repeated cycling.

General Synthesis of Charge Transport Materials

Charge transport materials as described herein can be prepared by the following multi-step synthesis. A person of ordinary skill in the art will recognize that alternative synthesis approaches can be used based on the teaching of the synthesis described herein.

Symmetrical charge transport materials can be prepared by the following procedure. In the first step a 9-fluorenone or a derivative compound reacts with an excess of hydrazine at 50-70° C. for 1-6 hours to produce a 9-fluorenone hydrazone compound or derivative thereof. Then, the 9-fluorenone hydrazone compound can be isolated and purified. In the next step, the 9-fluorenone hydrazone reacts with a linking compound having 2 aldehyde groups or ketone groups, such as OCH—CHO, a quinone derivative, or a diphenoquinone derivative, in a mole ratio of 2:1 (2 mole of hydrazine derivative with 1 mole of the linking compound). The desired product can be isolated and purified by recrystalization or/and column chromatography.

Unsymmetrical charge transport materials can be prepared by using an unsymmetrical linking compound such as 6-dimethyl-1, 4-benzoquinone. Alternatively, unsymmetrical charge transport materials can be prepared by the following procedure. In the first step, a first 9-fluorenone or a derivative thereof reacts with an excess of hydrazine at 50-70° C. for 1-6 hours to produce a first 9-fluorenone hydrazone compound or a derivative thereof. Then, the first 9-fluorenone hydrazone compound can be isolated and purified. In a subsequent step, a second 9-fluorenone derivative reacts with an excess of hydrazine at 50-70° C. for 1-6 hours to produce a second 9-fluorenone hydrazone derivative. Then, the second 9-fluorenone hydrazone derivative can be isolated and purified. In another step, the first 9-fluorenone hydrazone derivative reacts with a linking compound having 2 aldehyde groups or ketone groups, such as OCH—CHO, a quinone derivative, or a diphenoquinone derivative, in a mole ratio of 1:1 to form an 9-fluorenone azine compound having one aldehyde or ketone group. In the next step, the second 9-fluorenone hydrazone derivative reacts with the 9-fluorenone azine compound in a mole ratio of 1:1 to form the desired product. The desired product can be isolated and purified by recrystalization or/and column chromatography. A person or ordinary skill in the art can reduce the amount of symmetrical by-products, and these symmetrical by-product compounds can be separated in the purification steps.

The invention will now be described further by way of the following examples.

EXAMPLES

Example 1

Synthesis and Characterization Charge Transport Materials

This example described the synthesis and characterization of Compounds 2-13 in which the numbers refer to formula numbers above. The characterization involves chemical characterization of materials formed with the compounds. The electrostatic characterization of the compounds is described later. The synthesis of a reference charge transport compound is also described.

Preparation of (4-n-Butoxycarbonyl-9-fluorenylidene)malononitrile

A mixture of 9-fluorenone-4-carboxylic acid (70 g, 0.312 mole, from Sigma-Aldrich, Milwaukee, Wis.), n-butanol (480 g, 6.5 mole, from Fisher Scientific Company Inc., Hanover Park, Ill.), toluene (1000 ml), and concentrated sulfuric acid (4 ml) was added to a 2-liter round-bottom flask equipped with a mechanical stirrer, a reflux condenser, and a Dean Stark apparatus. With aggressive agitation, the solution was refluxed for 5 hours. During the 5-hour period, water (~6 g) was collected in the Dean Stark apparatus. The flask was cooled to room temperature. The solvents were evaporated, and the residue was added, with agitation, to 4-liter of a 3 wt. % aqueous solution of sodium bicarbonate. The solid was filtered off, washed with water until the pH of the washed water was neutral, and dried in the hood overnight. The product was n-butyl fluorenone-4-carboxylate ester. The yield was 70 g (80%). A $^1$H-NMR spectrum of n-butyl fluorenone-4-carboxylate ester was obtained in $CDCl_3$ with a 300 MHz NMR from Bruker Instrument and was characterized by the following chemical shifts ($\delta$, ppm): 0.87-1.09 (t, 3H); 1.42-1.70 (m, 2H); 1.75-1.88 (q, 2H); 4.26-4.64 (t, 2H); 7.29-7.45 (m, 2H); 7.46-7.58 (m, 1H); 7.60-7.68 (dd, 1H); 7.75-7.82 (dd, 1H); 7.90-8.00 (dd, 1H); and 8.25-8.35 (dd, 1H).

A mixture of 70 g (0.25 mole) of n-butyl fluorenone-4-carboxylate ester, 750 ml of absolute methanol, 37 g (0.55 mole) of malononitrile (from Sigma-Aldrich, Milwaukee, Wis.), 20 drops of piperidine (from Sigma-Aldrich, Milwaukee, Wis.) was added to a 2-liter, 3-neck round-bottom flask equipped with a mechanical stirrer and a reflux condenser. The solution was refluxed for 8 hours, and the flask was cooled to room temperature. The orange crude product was filtered, washed twice with 70 ml of methanol and once with 150 ml of water, and dried overnight in a hood. This orange crude product was recrystallized from a mixture of 600 ml of acetone and 300 ml of methanol using activated charcoal. The flask was placed at 0° C. for 16 hours. The crystals formed were filtered off and dried in a vacuum oven at 50° C. for 6 hours to obtain 60 g of pure (4-n-butoxycarbonyl-9-fluorenylidene)malononitrile. The melting point of the solid was found to be 99-100° C. A $^1$H-NMR spectrum of (4-n-butoxycarbonyl-9-fluorenylidene)malononitrile was obtained in $CDCl_3$ with a 300 MHz NMR from Bruker Instrument and was characterized by the following chemical shifts ($\delta$, ppm): 0.74-1.16 (t, 3H); 1.38-1.72 (m, 2H); 1.70-1.90 (q, 2H); 4.29-4.55 (t, 2H); 7.317.43 (m, 2H); 7.45-7.58 (m, 1H); 7.81-7.91 (dd, 1H); 8.15-8.25 (dd, 1H); 8.42-8.52 (dd, 1H); and 8.56-8.66 (dd, 1H).

Compound (2)

A mixture of 36 g of 9-fluorenone (0.2 mole, from Aldrich chemicals, Milwaukee, Wis.), 200 ml of ethanol, 12.82 g of anhydrous hydrazine (0.4 mole, from Aldrich Chemicals, Milwaukee, Wis.) was added to a 500 ml 3-neck round-bottom flask equipped with a mechanical stirrer and a reflux condenser. The flask was heated at 74° C. for 5 hours. After heating was completed, the solution was kept at 0° C. overnight. A yellow solid was filtered off, washed with 50 ml of ethanol, and dried at 50° C. in a vacuum oven for 8 hours. The yield was 35 g (92%). The $^1$H-NMR spectrum (300 MHz) of the product, 9-fluorenone hydrazone, in $CDCl_3$ was characterized by the following chemical shifts ($\delta$, ppm): 6.17-6.25 ($NH_2$, a broad singlet); and 7.21-7.94 (m, 8 aromatic protons).

A mixture of 4.85 g of 9-fluorenone hydrazone (0.025 mole, prepared in the previous step), 200 ml of ethanol, 1.35 g of 1, 4-benzoquinone (0.0125 mole, from Aldrich chemicals, Milwaukee, Wis.) and 7 drops of 37% aqueous hydrochloric acid was added to a 500 ml 3-neck round-bottom flask equipped with a reflux condenser and a mechanical stirrer. The mixture was refluxed for 5.5 hour. Compound (2) was filtered and dried at 50° C. in a vacuum oven for 8 hours. The yield was 2.3 g (40%).

Compound (3)

A mixture of 9-fluorenone-4-carboxylic acid, (70 g, 0.312 mole, from Sigma-Aldrich, Milwaukee, Wis.), ethyl alcohol (300 g, 6.5 mole, obtained from Aldrich, Milwaukee, Wis.), 1000 ml of toluene, and 4 ml of concentrated sulfuric acid was added to a 2-liter round-bottom flask equipped with a mechanical stirrer, a reflux condenser, and a Dean Stark apparatus. With aggressive agitation, the solution was refluxed for 5 hours. During the 5-hour period, water (about 6 g) was collected in the Dean Stark apparatus. The flask was cooled to room temperature. The solvents were evaporated and the residue was added, with agitation, to 4-liter of a 3 wt. % sodium bicarbonate aqueous solution. The solid was filtered, washed with water until the pH of the washed water was neutral, and dried in a fume hood overnight. The product was ethyl 9-fluorenone-4-carboxylate ester. The yield was 65 g (83%). The $^1$H-NMR spectrum (300 MHz) of the product in $CDCl_3$ was characterized by the following chemical shifts ($\delta$, ppm): 1.38-1.53 (t, 3H); 4.40-4.59 (q, 2H); and 7.30-8.33 (m, aromatic protons).

A mixture of ethyl 9-fluorenone-4-carboxylate ester (50.45 g, 0.2 mole, prepared in the previous step), 200 ml of ethanol, and anhydrous hydrazine (12.82 g, 0.4 mole, from Aldrich, Milwaukee, Wis.) was added to a 500 ml 3-neck round-bottom flask equipped with a mechanical stirrer and a reflux condenser. The flask was heated at 74° C. for 5 hours. After the heating was completed, the solution was kept at 0° C. overnight. A yellow solid was filtered, washed with 50 ml of ethanol, and dried at 50° C. in a vacuum oven for 8 hours. The yield was 40 g (76%).

To a 500 ml 3-neck round bottom flask equipped with a reflux condenser and a mechanical stirrer were added 6.35 g of fluorenone carboxylate ester hydrazine (0.025 mole, prepared in previous step), 200 ml of ethanol, 1.35 g of 1, 4-benzoquinone (0.0125 mole, obtained from Aldrich chemicals, Milwaukee, Wis.) and 7 drops of 37% aqueous HCl. The solution was refluxed for 5½ hour. The crude product was isolated and was recrystalized 4 times from tetrahydrofuran/ethanol with charcoal. The product was filtered and dried at 50° C. oven vacuum for 8 hours. 2.9 g were obtained (40% yield).

Compound (4)

Compound (4) was prepared similarly according to the procedure for Compound (3) except that n-butanol replaced ethyl alcohol. The $^1$H-NMR spectrum (300 MHz) of the product in $CDCl_3$ was characterized by the following chemical shifts ($\delta$, ppm): 0.95-1.06 (t, 6H); 1.42-1.59 (m, 4H); 1.73-1.89 (q, 4H); 4.38-4.50 (t, 4H); and 7.26-8.40 (m, aromatic protons).

Compound (5)

Compound (5) can be prepared similarly according to the procedure for Compound (2) except that 2, 6-dimethyl-1,4-benzoquinone (from Aldrich Chemicals, Milwaukee, Wis.) replaces 1,4-benzoquinone.

Compound (6)

Compound (6) was prepared similarly according to the procedure for Compound (3) except that 2, 6-dimethyl-1,4-benzoquinone replaced 1, 4-benzoquinone. The $^1$H-NMR spectrum (300 MHz) of the product in $CDCl_3$ was characterized by the following chemical shifts ($\delta$, ppm): 1.39-1.52 (t, 6H); 4.40-4.58 (q, 4H); and 7.26-8.42 (m, aromatic protons).

Compound (7)

Compound (7) was prepared similarly according to the procedure for Compound (4) except 2, 6-dimethyl-1, 4-benzoquinone replaced 1, 4-benzoquinone. The $^1$H-NMR spectrum (300 MHz) of the product in $CDCl_3$ was characterized by the following chemical shifts ($\delta$, ppm): 0.92-1.08 (t, 6H); 1.40-1.62 (m, 4H); 1.72-1.89 (q, 4H); 4.36-4.51 (t, 4H); and 7.21-8.46 (m, aromatic protons).

Compound (8)

Compound (8) can be prepared similarly according to the procedure for Compound (2) except that duroquinone (from Aldrich Chemicals, Milwaukee, Wis.) replaces 1, 4-benzoquinone.

Compound (9)

Compound (9) can be prepared similarly according to the procedure for Compound (3) except that duroquinone (from Aldrich Chemicals, Milwaukee, Wis.) replaces 1, 4-benzoquinone.

Compound (10)

Compound (10) can be prepared similarly according to the procedure for Compound (4) except that duroquinone (from Aldrich Chemicals, Milwaukee, Wis.) replaces 1, 4-benzoquinone.

Compound (11)

Compound (11) was prepared similarly according to the procedure for Compound (3) except that 3,3', 5,5'-tetramethyldiphenoquinone replaced 1,4-benzoquinone. The yield was 5.0 g (34%). The $^1$H-NMR spectrum (300 MHz) of the product in $CDCl_3$ was characterized by the following chemical shifts ($\delta$, ppm): 1.41-1.52 (t, 6H); 4.42-4.57 (q, 4H); and 7.27-8.41 (m, aromatic protons).

Compound (12)

Compound (12) was prepared similarly according to the procedure for Compound (4) except that 3,3', 5,5'-tetramethyldiphenoquinone replaced 1,4-benzoquinone. The $^1$H-NMR spectrum (300 MHz) of the product in $CDCl_3$ was characterized by the following chemical shifts ($\delta$, ppm): 0.94-1.06 (t, 6H); 1.40-1.60 (m, 4H); 1.73 1.89 (m, 4H); 4.37-4.50 (t, 4H); and 7.27-8.40 (m, aromatic protons).

Compound (13)

Compound (13) can be prepared similarly according to the procedure for Compound (2) except that 3,3', 5,5'-tetramethyldiphenoquinone replaces 1,4-benzoquinone.

Example 2

Preparation of Organophotoreceptors

This example describes the preparation of 9 organophotoreceptors with Compounds (4), (6), (7), (11), (12) and three comparative organophotoreceptor prepared with a comparative electron transport compound, (4-n-butoxycarbonyl-9-fluorenylidene)malononitrile.

Comparative Sample A

Comparative Sample A was a single layer organophotoreceptor having a 76.2 micron (3 mil) thick polyester substrate with a layer of vapor-coated aluminum (commercially obtained from CP Films, Martinsville, Va.). The coating solution for the single layer organophotoreceptor was prepared by pre-mixing 2.4 g of 20 wt. % (4-n-butoxycarbonyl-9-fluorenylidene)malononitrile in tetrahydrofuran, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base containing 20 wt. % of titanyl oxyphthalocyanine and a polyvinyl butyral resin (BX-5, commercially obtained from Sekisui Chemical Co. Ltd., Japan) at a weight ratio of 2.3:1 was then added to the above mixture. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of methylethylketone on a horizontal sand mill (model LMC12 DCMS, commercially obtained from Netzsch Incorporated, Exton, Pa.) with 0.8 mm zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes. The dry coating thickness was 10 µm±0.5 µm.

Sample 1

Sample 1 was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20 wt. % Compound (4) in tetrahydrofuran, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 20 wt. % of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes. The dry coating thickness was 10 μm±0.5 μm.

Sample 2

Sample 2 was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20 wt. % Compound (7) in tetrahydrofuran, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 19% of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes. The dry coating thickness was 10 μm±0.5 μm.

Sample 3

Sample 3 was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20 wt. % Compound (6) in 1,1,2-trichloroethane (obtained from Aldrich Chemicals, Milwaukee, Wis.), 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 19% of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing on a mechanical shaker for ~1 hour, the single layer coating solution was coated onto the substrate described above using a knife coater with a gap space of 94 micron followed by drying in an oven at 110° C. for 5 minutes. The dry coating thickness was 10 μm±0.5 μm.

Sample 4

Sample 4 was a single layer organophotoreceptor having a 76.2 micron (3 mil) thick polyester substrate having a layer of vapor-coated aluminum (commercially obtained from CP Films, Martinsville, Va.). The coating solution for the single layer organophotoreceptor was prepared by pre-mixing 2.4 g of 20 wt. % 4-n-butoxycarbonyl-9-fluorenylidene)malononitrile in tetrahydrofuran, 6.66 g of 25 wt. % Compound (4) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 20 wt. % of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing on a mechanical shaker for ~1 hour, the single layer coating solution was coated onto the substrate described above using a knife coater with a gap space of 94 microns followed by drying in an oven at 110° C. for 5 minutes. The dry coating thickness was 10 μm±0.5 μm.

Comparative Sample B

Comparative Example B was a single layer organophotoreceptor coated on a 30 mm diameter anodized aluminum drum substrate. The coating solution for the single layer organophotoreceptor was prepared by pre-mixing 2.4 g of 20 wt. % (4-n-butoxycarbonyl-9-fluorenylidene)malononitrile in tetrahydrofuran, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base containing 20 wt. % of titanyl oxyphthalocyanine and a polyvinyl butyral resin (BX-5, commercially obtained from Sekisui Chemical Co. Ltd., Japan) at a weight ratio of 2.3:1 was then added to the above mixture. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of methylethylketone on a horizontal sand mill (model LMC12 DCMS, commercially obtained from Netzsch Incorporated, Exton, Pa.) with 0.8 mm zirconium beads using recycle mode for 4 hours.

After mixing the solution on a mechanical shaker for ~1 hour, the single layer coating solution was ring coated onto the 30 mm diameter anodized aluminum drum at a rate of 112 mm/min and followed by drying in an oven at 110° C. for 5-10 minutes. The dry photoconductor film thickness was 16 um±0.5 um.

Comparative Sample C

Comparative Sample C was made similar to Comparative Sample B except the ring coating rate was increased to produce a dry film thickness of 20 μm.

Sample 5

Sample 5 was a single layer organophotoreceptor coated on a 30 mm diameter anodized aluminum drum substrate. The coating solution for the single layer organophotoreceptor was prepared by pre-mixing 2.4 g of 20 wt. % Compound (11) in 1,1,2-trichloroethan, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 20 wt. % of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours.

After mixing the solution on a mechanical shaker for ~1 hour, the single layer coating solution was ring coated onto the 30 mm diameter anodized aluminum drum at a rate of 112 mm/min and followed by drying in an oven at 110° C. for 5-10 minutes. The dry photoconductor film thickness was 16 um±0.5 um.

Sample 6

Sample 6 was made similar to Sample 5 except the ring coating rate was increased to produce a dry film thickness of 20 μm.

Sample 7

Sample 7 was a single layer organophotoreceptor coated on a 30 mm diameter anodized aluminum drum substrate. The coating solution for the single layer organophotoreceptor was prepared by pre-mixing 2.4 g of 20 wt. % Compound (12) in tetrahydrofuran, 6.66 g of 25 wt. % MPCT-10 (a charge transfer material, commercially obtained from Mitsubishi Paper Mills, Tokyo, Japan) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 20 wt. % of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing the solution on a mechanical shaker for ~1 hour, the single layer coating solution was ring coated onto the 30 mm diameter anodized aluminum drum at a rate of 112 mm/min and followed by drying in an oven at 110° C. for 5-10 minutes. The dry photoconductor film thickness was 16 um±0.5 um.

Sample 8

Sample 8 was made similarly to Sample 7 except the ring coating rate was increased to produce a dry film thickness of 20 μm.

Sample 9

Sample 9 was a single layer organophotoreceptor coated on a 30 mm diameter anodized aluminum drum substrate. The coating solution for the single layer organophotoreceptor was prepared by pre-mixing 2.4 g of 20 wt. % 4-n-butoxycarbonyl-9-fluorenylidene)malononitrile in tetrahydrofuran, 6.66 g of 25 wt. % Compound (12) in tetrahydrofuran, 7.65 g of 12 wt. % polyvinyl butyral resin (BX-1, commercially obtained from Sekisui Chemical Co. Ltd., Japan) in tetrahydrofuran. A 0.74 g quantity of a CGM mill-base was then added to the above mixture. The CGM mill-base contained 20 wt. % of titanyl oxyphthalocyanine and a polyvinyl butyral resin (BX-5, commercially obtained from Sekisui Chemical Co. Ltd., Japan) at a ratio of 2.3:1. The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 0.8 mm zirconium beads using recycle mode for 4 hours. After mixing the solution on a mechanical shaker for ~1 hour, the single layer coating solution was ring coated onto the 30 mm diameter anodized aluminum drum at a rate of 112 mm/min and followed by drying in an oven at 110° C. for 5-10 minutes. The dry photoconductor film thickness was 16 um±0.5 um.

Example 3

Electrostatic Testing and Properties of Organophotoreceptors

This example provides results of electrostatic testing on the organophotoreceptor samples formed as described in Example 1.

Electrostatic cycling performance of organophotoreceptors described herein with azine compounds can be determined using in-house designed and developed test beds that are capable of testing, for example, the sample strips wrapped around a 160 mm drum or 30 mm aluminum drums. The results on these samples are indicative of results that would be obtained with other support structures, such as belts, drums and the like, for supporting the organophotoreceptors.

For testing using a 160 mm drum, three coated sample strips, each measuring 50 cm long by 8.8 cm wide, are fastened side-by-side and completely around an aluminum drum (50.3 cm circumference). In some embodiments, at least one of the strips is a comparative example that is precision web coated and used as an internal reference point. In this electrostatic cycling tester, the drum rotated at a rate of 8.13 cm/sec (3.2 ips), and the location of each station in the tester (distance and elapsed time per cycle) is given as shown in the following table.

TABLE 1

Electrostatic test stations around the 160 mm drum at 8.13 cm/sec.

| Station | Degrees | Total Distance, cm | Total Time, sec |
|---|---|---|---|
| Front erase bar edge | 0° | Initial, 0 cm | Initial, 0 s |
| Erase Bar | 0-7.2° | 0-1.0 | 0-0.12 |
| Scorotron Charger | 113.1-135.3° | 15.8-18.9 | 1.94-2.33 |
| Laser Strike | 161.0° | 22.5 | 2.77 |
| Probe #1 | 181.1° | 25.3 | 3.11 |
| Probe #2 | 251.2° | 35.1 | 4.32 |
| Erase bar | 360° | 50.3 | 6.19 |

The erase bar is an array of laser emitting diodes (LED) with a wavelength of 720 nm. that discharges the surface of the organophotoreceptor. The scorotron charger comprises a wire that permits the transfer of a desired amount of charge to the surface of the organophotoreceptor.

From the above table, the first electrostatic probe (TREK 344™ electrostatic meter, Trek, Inc. Medina, N.Y.) is located 0.34 s after the laser strike station and 0.78 s after the scorotron while the second probe (TREK™ 344 electrostatic meter) is located 1.21 s from the first probe and 1.99 s from the scorotron. All measurements are performed at ambient temperature and relative humidity.

Electrostatic cycling performance of organophotoreceptors described herein with fluoran compounds can be determined using in-house designed and developed test bed. Electrostatic evaluation on the 30 mm drum test bed is designed to accelerate electrostatic fatigue during extended cycling by increasing the charge-discharge cycling frequency and decreasing the recovery time as compared to drum test beds with longer process speeds. The location of each station in the tester (distance and elapsed time per cycle) is given as follows.

Electrostatic measurements were obtained as a compilation of several runs on the test station. The first three diagnostic tests (prodtest initial, VlogE initial, dark decay initial) are designed to evaluate the electrostatic cycling of a new, fresh sample and the last three, identical diagnostic test (prodtest final, VlogE final, dark decay final) are run after cycling of the sample. In addition, measurements were made periodically during the test, as described under "longrun" below. The laser is operated at 780 nm wavelength, 600 dpi, 50 micron spot size, 60 nanoseconds/pixel expose time, 1,800 lines per second scan speed, and a 100% duty cycle. The duty cycle is the percent exposure of the pixel clock period, i.e., the laser is on for the full 60 nanoseconds per pixel at a 100% duty cycle.

Electrostatic Test Suite:

1) PRODTEST: Charge acceptance ($V_{acc}$) and discharge voltage ($V_{dis}$) were established by subjecting the samples to corona charging (erase bar always on) for three complete drum revolutions (laser off); discharged with the laser @ 780 nm & 600 dpi on the forth revolution (50 um spot size, expose 60 nanoseconds/pixel, run at a scan speed of 1,800 lines per second, and use a 100% duty cycle); completely charged for the next three revolutions (laser off); discharged with only the erase lamp @ 720 nm on the eighth revolution (corona and laser off) to obtain residual voltage ($V_{res}$); and, finally, completely charged for the last three revolutions (laser off). The contrast voltage ($V_{con}$) is the difference between $V_{acc}$ and $V_{dis}$ and the functional dark decay ($V_{dd}$) is the difference in charge acceptance potential measured by probes #1 and #2.

2) VLOGE: This test measures the photoinduced discharge of the photoconductor to various laser intensity levels by monitoring the discharge voltage of the sample as a function of the laser power (exposure duration of 50 ns) with fixed exposure times and constant initial potentials. This test measures the photoinduced discharge of the photoconductor to various laser intensity levels by monitoring the discharge voltage of the sample as a function of the laser power (exposure duration of 50 ns) with fixed exposure times and constant initial potentials. The functional photosensitivity, $S_{780nm}$, and operational power settings can be determined from this diagnostic test.

3) DARK DECAY: This test measures the loss of charge acceptance in the dark with time without laser or erase illumination for 90 seconds and can be used as an indicator of i) the injection of residual holes from the charge generation layer to the charge transport layer, ii) the thermal liberation of trapped charges, and iii) the injection of charge from the surface or aluminum ground plane.

4) LONGRUN: The sample was electrostatically cycled for 500 drum revolutions according to the following sequence per each sample-drum revolution. The sample was charged by the corona, the laser was cycled on and off (80-100° sections) to discharge a portion of the sample and, finally, the erase lamp discharged the whole sample in preparation for the next cycle. The laser was cycled so that the first section of the sample was never exposed, the second section was always exposed, the third section was never exposed, and the final section was always exposed. This pattern was repeated for a total of 500 drum revolutions, and the data was recorded periodically, after every 25th cycle.

5) After the LONGRUN test, the PRODTEST, VLOGE, DARK DECAY diagnostic tests were run again.

The following Tables shows the results from the prodtest initial and prodtest final diagnostic tests. The values for the charge acceptance voltage ($V_{acc}$, probe #1 average voltage obtained from the third cycle), discharge voltage ($V_{dis}$, probe #1 average voltage obtained from the fourth cycle) are reported for the initial and final cycles.

TABLE 2

Dry Electrostatic Test Results after 500 cycles.

| Sample | Prodtest Initial | | | | | Prodtest after 500 cycles | | | |
|---|---|---|---|---|---|---|---|---|---|
| | $V_{acc}$ | $V_{dis}$ | $V_{con}$ | $S_{780\,nm}$ | $V_{res}$ | $V_{acc}$ | $V_{dis}$ | $V_{con}$ | $V_{res}$ |
| Sample 1 | 833 | 88 | 745 | 222 | 33 | 563 | 67 | 496 | 32 |
| Sample 2 | 999 | 99 | 900 | 236 | 37 | 764 | 80 | 684 | 32 |
| Sample 3 | 1145 | 126 | 1019 | 199 | 45 | 952 | 156 | 796 | 45 |
| Sample 4 | 1009 | 993 | 16 | NA | 733 | 1122 | 1083 | 39 | 886 |
| Sample 5 | 1120 | 86 | 1034 | 236 | 34 | 858 | 67 | 791 | 31 |
| Sample 6 | 1180 | 82 | 1098 | 222 | 30 | 956 | 71 | 885 | 29 |
| Sample 7 | 1187 | 114 | 1073 | 236 | 44 | 900 | 92 | 808 | 41 |
| Sample 8 | 1292 | 126 | 1166 | 236 | 50 | 975 | 103 | 872 | 46 |
| Sample 9 | 1736 | 1725 | 11 | NA | 1601 | 1813 | 1744 | 69 | 1631 |
| Comparative Sample A | 905 | 61 | 844 | 210 | 21 | 618 | 58 | 560 | 22 |
| Comparative Sample B | 967 | 54 | 913 | 236 | 21 | 652 | 55 | 597 | 30 |
| Comparative Sample C | 1266 | 62 | 1204 | 290 | 25 | 864 | 63 | 801 | 34 |

In the above table, the radiation sensitivity (Sensitivity at 780 nm in m²/J) of the xerographic process was determined from the information obtained during the VLOGE diagnostic run by calculating the reciprocal of the product of the laser power required to discharge the photoreceptor to 12 of its initial potential, the exposure duration, and 1/spot size.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:
   (a) a charge transport material having the formula

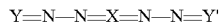
   Y=N—N=X=N—N=Y' where Y and Y' comprise, each independently, a 9-fluorenylidene group and X is a conjugated linking group that allows the delocalization of pi electrons over at least Y and Y', wherein X is selected from the group consisting of a 1,2-ethanediylidene group, a 1,4-phenylenedimethylidyne group, a 2,4-cyclohexadienylidene group, a 2,5-cyclohexadienylidene group, a bicyclohexylidene-2,5,2',5'-tetraene group, a bicyclohexylidene-2,4,2',4'-tetraene group, a combination thereof, and a $(C_6R_1R_2R_3R_4)_n$ group, where the $C_6$ group is a cyclohexadienylidene group with substituents $R_1R_2R_3R_4$; n is an integer between 1 and 20, inclusive; and $R_1$, $R_2$, $R_3$, and $R_4$, each independently, are a hydrogen, a halogen, an amino group, a nitro group, a cyano group, an alkyl group, an alkenyl group, a heterocyclic group, an aromatic group, or part of a ring group; and
   (b) a charge generating compound.

2. The organophotoreceptor according to claim 1 wherein the $C_6R_1R_2R_3R_4$ group has one of the following formulae:

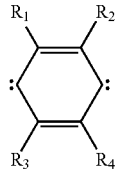 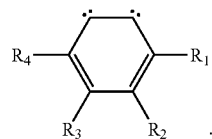

3. The organophotoreceptor according to claim 1 wherein Y and Y', each independently, have the following formula:

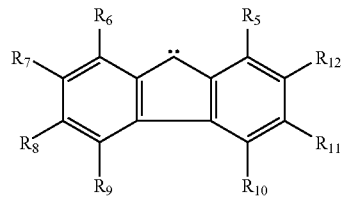

where $R_5$, $R_6$, $R_7$, $R_8$, $R_9$, $R_{10}$, $R_{11}$, and $R_{12}$, each independently, are a hydrogen, a halogen, a hydroxyl group, a thiol group, a carboxyl group, an amino group, a nitro group, a cyano group, an alkyl group, an alkenyl group, a heterocyclic group, an aromatic group, or part of a ring group.

4. The organophotoreceptor according to claim 1 wherein the charge transport material is selected from the group consisting of:

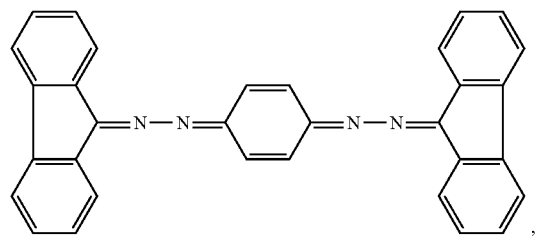

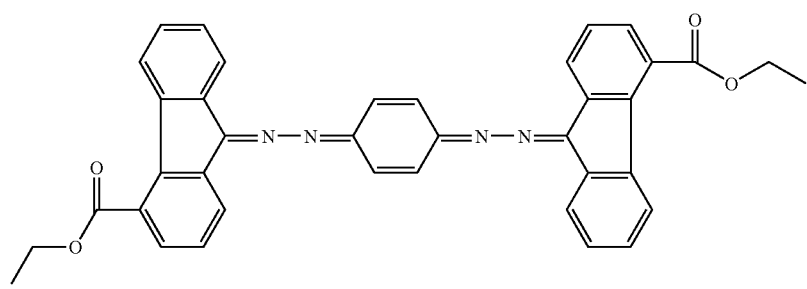

-continued
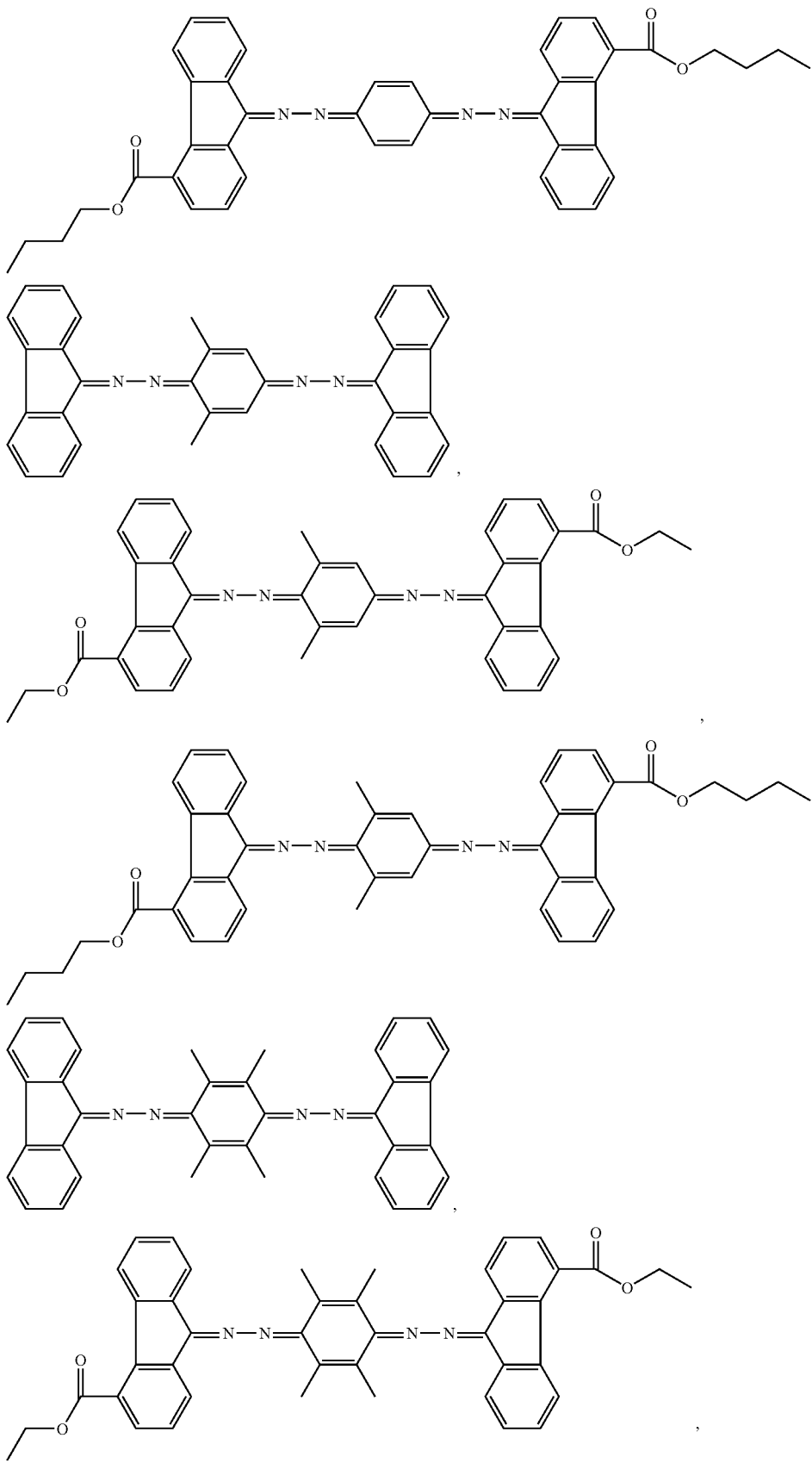

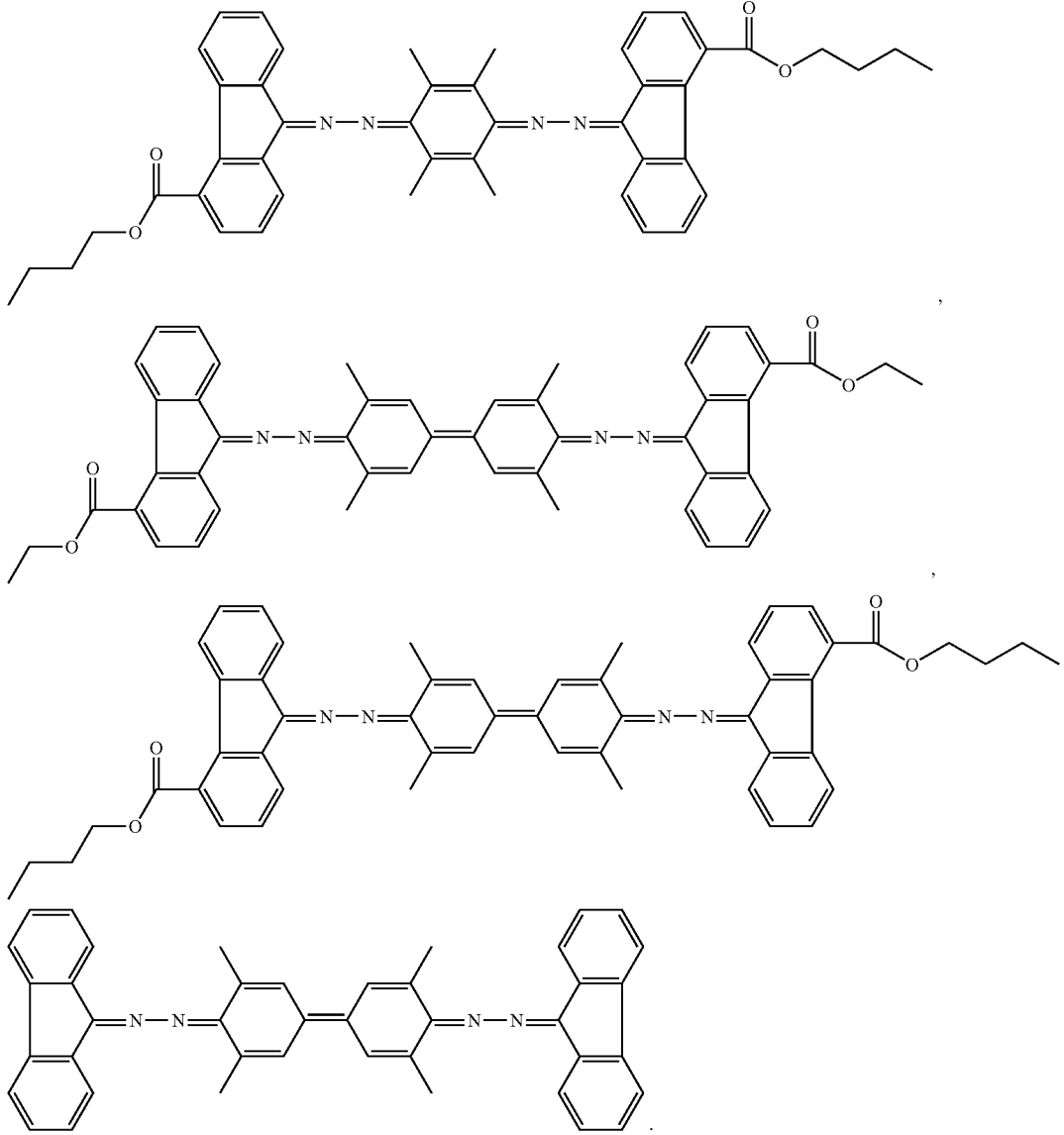

, and

5. The organophotoreceptor according to claim 1 comprising:
   (a) a charge transport layer comprising the charge transport material and a polymeric binder; and
   (b) a charge generating layer comprising the charge generating compound and a polymeric binder.

6. The organophotoreceptor according to claim 1 wherein the photoconductive element further comprises a second charge transport material.

7. The organophotoreceptor according to claim 6 wherein the second charge transport material comprises a charge transport compound.

8. The organophotoreceptor according to claim 1 wherein the organophotoreceptor is in the form of a drum or a flexible belt.

9. An electrophotographic imaging apparatus comprising:
   (a) a light imaging component; and
   (b) an organophotoreceptor oriented to receive light from the light imaging component, the organophotoreceptor comprising an electrically conductive substrate and a photoconductive element on the electrically conductive substrate, the photoconductive element comprising:
      (i) a charge transport material having the formula $$Y\!=\!N\!-\!N\!=\!X\!=\!N\!-\!N\!=\!Y'$$

where Y and Y' are, each independently, a 9-fluorenylidene group and X is a conjugated linking group that allows the delocalization of pi electrons over at least Y and Y'; wherein X is selected from the group consisting of a 1,2-ethanediylidene group, a 1,4-phenylenedimethylidyne group, a 2,4-cyclohexadienylidene group, a 2,5-cyclohexadienylidene group, a bicyclohexylidene-2,5,2',5'-tetraene group, a bicyclohecxylidene-2,4,2',4'-tetraene group, a combination thereof, and a $(C_6R_1R_2R_3R_4)_n$ group, where the C6 group is a cyclohexadienylidene group with substituents $R_1R_2R_3R_4$; n is an integer between 1 and 20, inclusive; and $R_1$, $R_2$, $R_3$, and $R_4$, each independently, are a hydrogen, a halogen, an amino group, a nitro group, a cyano group, an alkyl group, an alkenyl group, a heterocyclic group, an aromatic group, or part of a ring group; and (ii) a charge generating compound.

10. The elecrophotographic imaging apparatus of claim 9 further comprising a toner dispenser.

11. The electrophotographic imaging apparatus of claim 9 wherein the organophotoreceptor further comprises a second charge transport material.

12. The electrophotographic imaging apparatus according to claim 11 wherein the second charge transport material comprises a charge transport compound.

13. The electrophotographic imaging apparatus according to claim 9 wherein the $C_6R_1R_2R_3R_4$ group has one of the following formulae:

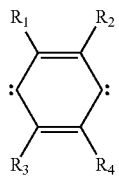 or 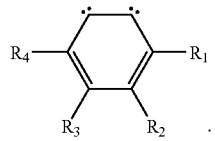

14. The electrophotographic imaging apparatus according to claim 9 wherein Y and Y', each independently, have the following formula:

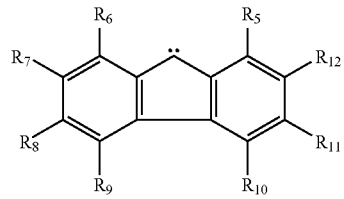

where $R_5$, $R_6$, $R_7$, $R_8$, $R_9$, $R_{10}$, $R_{11}$, and $R_{12}$, each independently, are a hydrogen, a halogen, a hydroxyl group, a thiol group, a carboxyl group, an amino group, a nitro group, a cyano group, an alkyl group, an alkenyl group, a heterocyclic group, an aromatic group, or part of a ring group.

15. The electrophotographic imaging apparatus of claim 9 wherein the charge transport material is selected from the group consisting of:

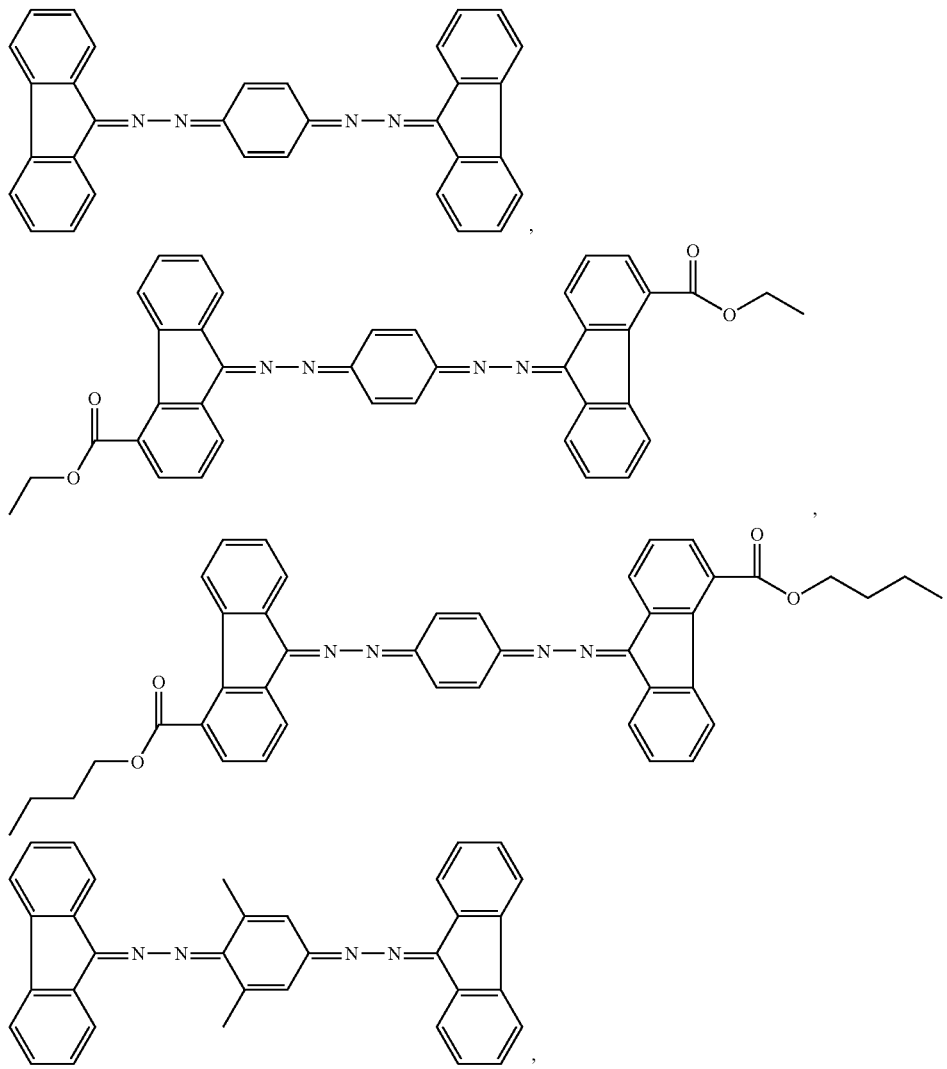

-continued
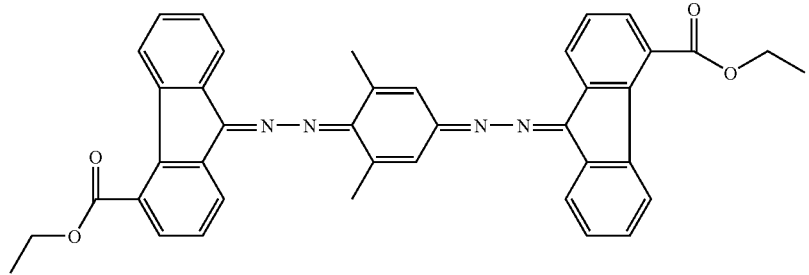
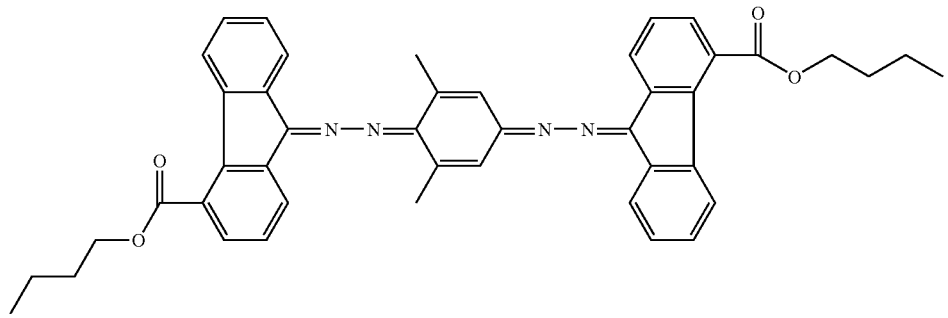
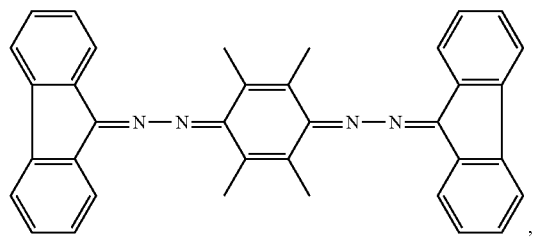
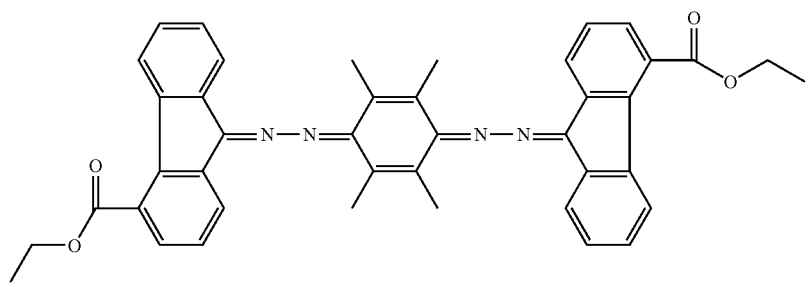
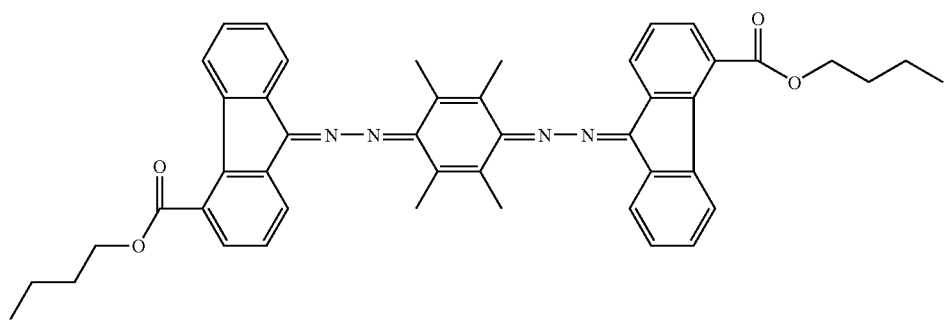

-continued

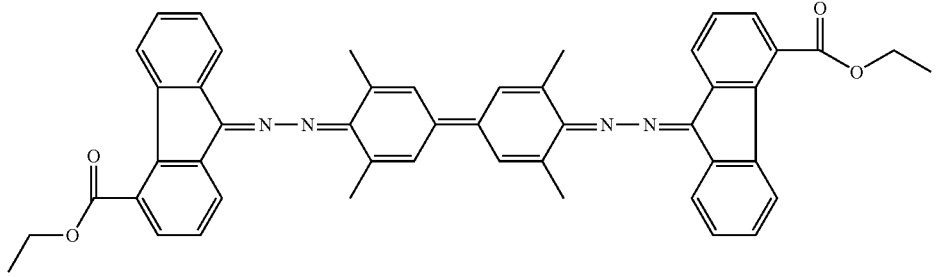

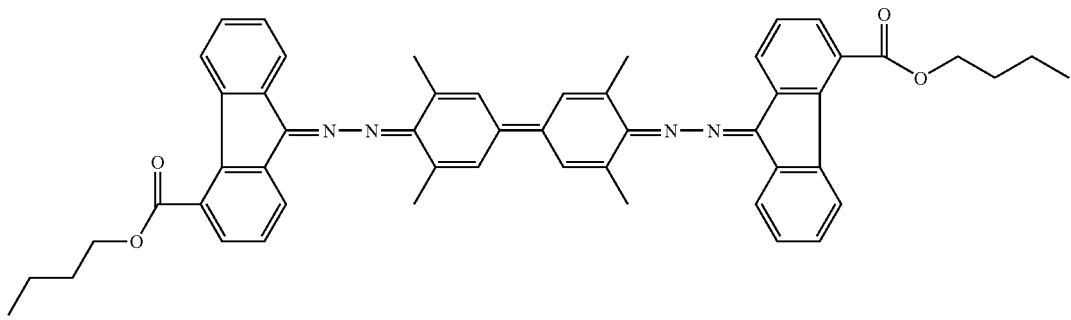
, and

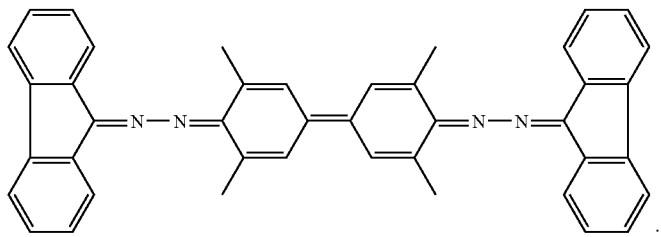
.

16. A charge transport material having the formula

Y=N—N=X=N—N=Y' where Y and Y' are, each independently, a 9-fluorenylidene group and X is a conjugated linking group that allows the delocalization of pi electrons over at least Y and Y', wherein X is selected from the group consisting of a 1,2-ethanediylidene group, a 1,4-phenylenedimethylidyne group, a 2,4-cyclohexadienylidene group, a 2,5-cyclohexadienylidene group, a bicyclohexylidene-2,5,2',5'-tetraene group, a bicyclohexylidene-2,4,2',4'-tetraene groups, a combination thereof, and a $(C_6R_1R_2R_3R_4)_n$ group, where the $C_6$ group is a cyclohexadienylidene group with substituents $R_1R_2R_3R_4$; n is an integer between 1 and 20, inclusive; and $R_1$, $R_2$, $R_3$, and $R_4$, each independently, are a hydrogen, a halogen, an wino group, a nitro group, a cyano group, an alkyl group, a alkenyl group, a heterocyclic group, an aromatic group, or pan of a ring group.

17. The charge transport material according to claim 16 wherein the $C_6R_1R_2R_3R_4$ group has one of the following formulae:

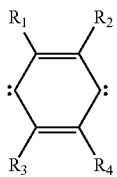 or 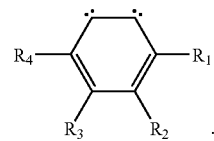

18. The charge transport material according to claim 16 wherein Y and Y', each independently, have the following formula

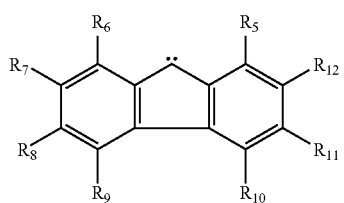

where $R_5$, $R_6$, $R_7$, $R_8$, $R_9$, $R_{10}$, $R_{11}$, and $R_{12}$, each independently, are a hydrogen, a halogen, a hydroxyl group, a thiol group, a carboxyl group, a amino group, a nitro group, a cyano group, an alkyl group, an alkenyl group, a heterocyclic group, an aromatic group, or part of a ring group.
19. The charge transport material of claim 16 wherein the charge transport material is selected from the group consisting of:
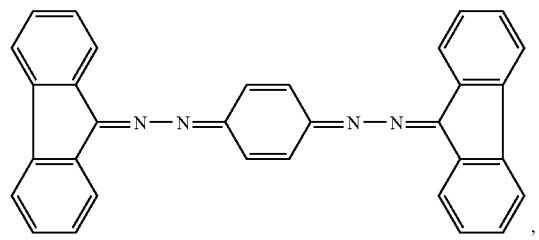
,
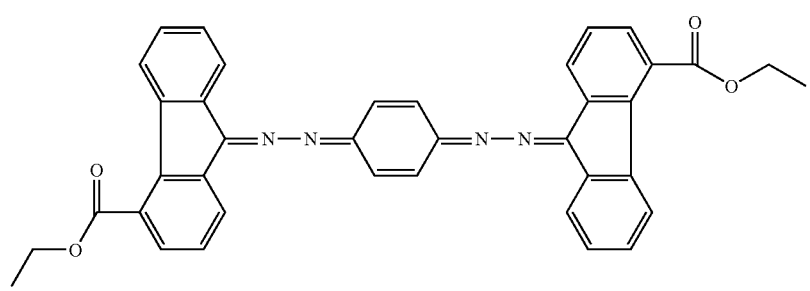
,
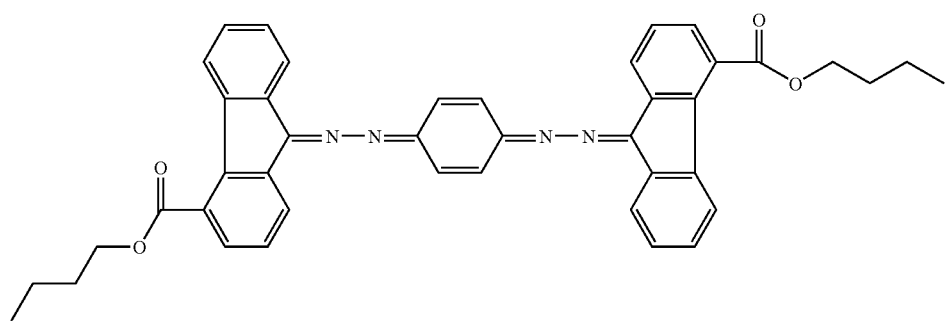
,
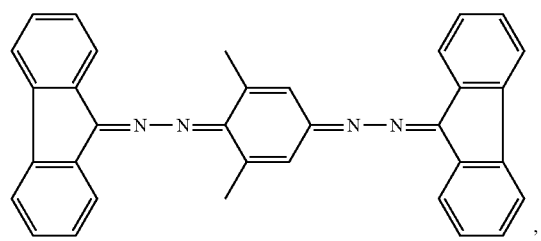
,
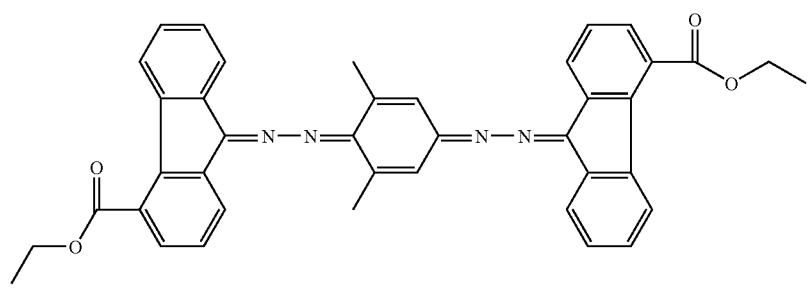
, -continued
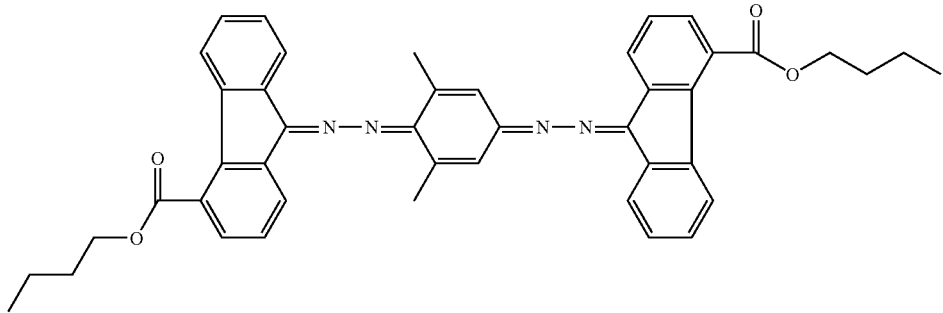
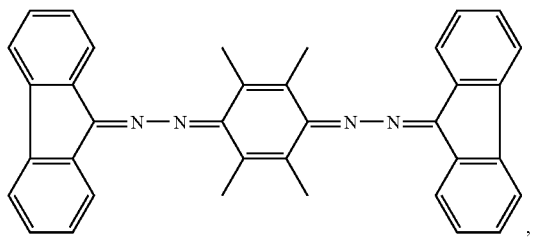
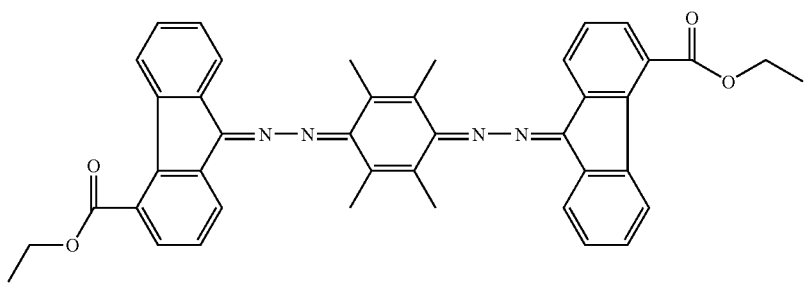
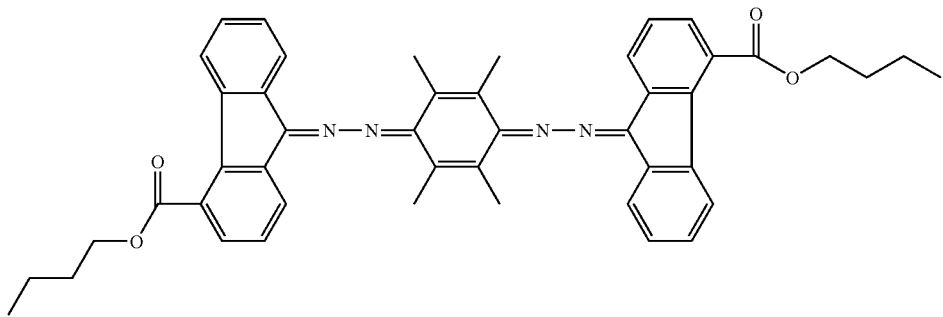
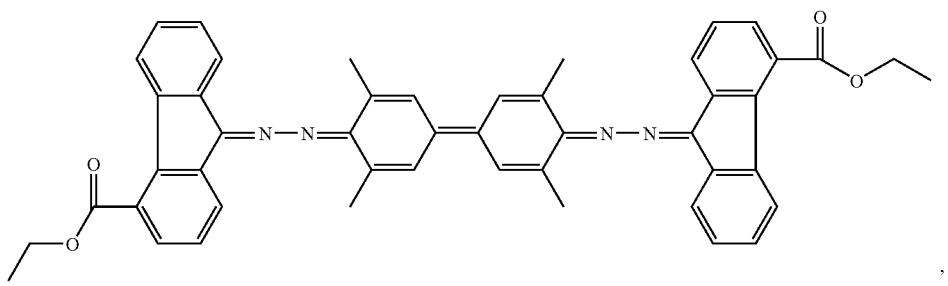

-continued
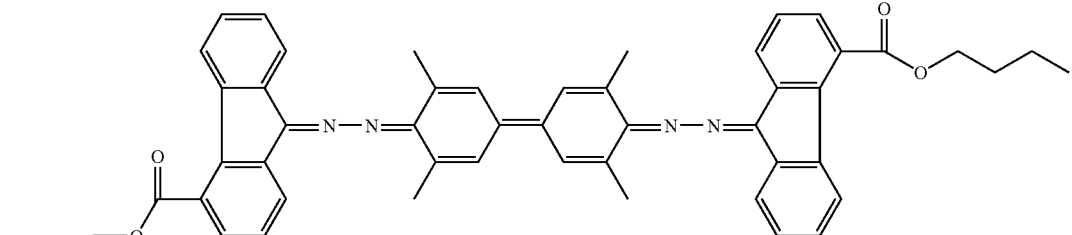
, and
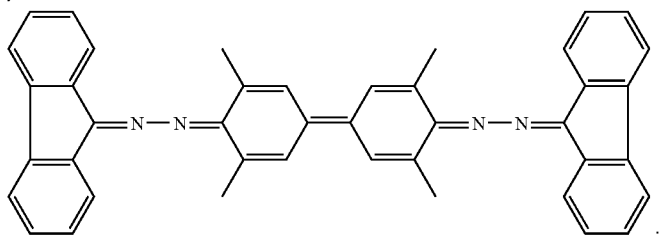
* * * * *